(12) United States Patent
Raczkowski et al.

(10) Patent No.: US 9,126,924 B2
(45) Date of Patent: Sep. 8, 2015

(54) CHEMICAL COMPOSITION

(75) Inventors: Henry Raczkowski, Salem, MA (US); D. Andrew Dineen, Jr., Melrose, MA (US); Daniel D'Auge, Union City, NJ (US)

(73) Assignee: THE CHARLES STARK DRAPER LABORATORY, INC., Cambridge, MA (US)

( * ) Notice: Subject to any disclaimer, the term of this patent is extended or adjusted under 35 U.S.C. 154(b) by 270 days.

(21) Appl. No.: 13/491,469

(22) Filed: Jun. 7, 2012

(65) Prior Publication Data

US 2013/0331589 A1     Dec. 12, 2013

(51) Int. Cl.
| | | |
|---|---|---|
| *C07C 69/017* | (2006.01) | |
| *C07C 69/24* | (2006.01) | |
| *C07C 271/44* | (2006.01) | |
| *C07C 271/58* | (2006.01) | |
| *C07C 69/50* | (2006.01) | |

(52) U.S. Cl.
CPC ............. *C07C 69/24* (2013.01); *C07C 69/017* (2013.01); *C07C 69/50* (2013.01); *C07C 271/44* (2013.01); *C07C 271/58* (2013.01)

(58) Field of Classification Search
None
See application file for complete search history.

(56) References Cited

U.S. PATENT DOCUMENTS

| | | | |
|---|---|---|---|
| 1,074,966 A * | 10/1913 | Merling | ............... 560/132 |
| 4,036,773 A | 7/1977 | Okorodudu | |
| 4,456,555 A | 6/1984 | Goel et al. | |
| 4,835,304 A | 5/1989 | Williams | |
| 5,177,252 A | 1/1993 | Williams | |
| 5,248,432 A | 9/1993 | Williams | |
| 6,103,927 A * | 8/2000 | De Castro Loureiro Barreto Rosa et al. | ............... 560/207 |
| 6,767,872 B2 | 7/2004 | Williams | |
| 7,081,440 B2 | 7/2006 | Navarrini et al. | |
| 8,299,004 B2 | 10/2012 | Tsubouchi | |
| 2007/0154708 A1 | 7/2007 | Wilson et al. | |
| 2007/0197408 A1 | 8/2007 | Holt | |
| 2008/0176775 A1 | 7/2008 | Wright et al. | |
| 2010/0120642 A1 | 5/2010 | Miller et al. | |
| 2010/0187481 A1 | 7/2010 | Bodesheim et al. | |
| 2013/0035268 A1 | 2/2013 | Zehler | |

FOREIGN PATENT DOCUMENTS

CN            1570047 A  *  1/2005   ........... C10M 135/10

OTHER PUBLICATIONS

Purdie, T., The action of metallic alkylates on mixtures of ethereal salts with alcohols, 1887, Journal of the Chemical Society, No. 51, pp. 627-634.*

* cited by examiner

*Primary Examiner* — Yate K Cutliff
(74) *Attorney, Agent, or Firm* — Lando & Anastasi, LLP

(57) ABSTRACT

Chemical compositions, lubricant compositions, and methods of using the same are provided. The lubricant composition may comprise at least on carrier. In certain methods, the lubricant composition may be provided to at least one surface, wherein the lubricant composition reduces a coefficient of friction of the at least one surface. In certain methods, the lubricant composition may be provided to at least one surface, wherein the lubricant composition reduces wear of the at least one surface.

6 Claims, 4 Drawing Sheets

CHEMICAL COMPOSITION

FIELD OF THE TECHNOLOGY

Aspects relate generally to compounds and lubricant compositions. Further aspects relate generally to systems and methods comprising the compounds and the lubricant compositions.

SUMMARY

In accordance with one or more embodiments, a compound comprising a formula:

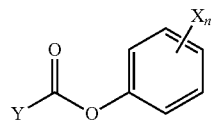

is provided, wherein: $X_n$ represents $(C_1\text{-}C_6)$alkyl, $(C_1\text{-}C_6)$alkoxy, or heteroatom, and n is 0-5; Y represents $(C_1\text{-}C_{30})$alkyl, aryl, heteroaryl, $NR^aR^b$, or heteroatom, wherein $(C_1\text{-}C_{30})$alkyl, aryl, and heteroaryl are substituted with 0-3 occurrences of $R^4$; $R^a$ and $R^b$ represent $(C_1\text{-}C_6)$alkyl, $(C_1\text{-}C_6)$alkoxy, aryl, or heteroaryl; $R^4$ represents $(C_1\text{-}C_6)$alkyl, $(C_1\text{-}C_6)$alkoxy, $-C(O)OR^5$, aryl, or heteroaryl; and $R^5$ is 2,4,6-trimethylphenyl. In certain embodiments Y represents $(C_1\text{-}C_{30})$alkyl or $NR^aR^b$; wherein $(C_1\text{-}C_{30})$alkyl is substituted with 0-1 occurrences of $R^4$; $R^a$ and $R^b$ represent $(C_1\text{-}C_6)$alkyl, $(C_1\text{-}C_6)$alkoxy, aryl, or heteroaryl; and $R^4$ represents $(C_1\text{-}C_6)$alkyl, $(C_1\text{-}C_6)$alkoxy, or $-C(O)OR^5$; and $R^5$ is 2,4,6-trimethylphenyl.

In certain aspects, Y represents $(C_1\text{-}C_{30})$alkyl, wherein $(C_1\text{-}C_{30})$alkyl is substituted with 0-1 occurrences of $R^4$, $R^4$ represents $(C_1\text{-}C_6)$alkyl or $-C(O)OR^5$, and $R^5$ is 2,4,6-trimethylphenyl. In certain aspects, Y represents $(C_1\text{-}C_{30})$alkyl, wherein $(C_1\text{-}C_{30})$alkyl is substituted with 0-1 occurrences of $R^4$ and $R^4$ is $(C_1\text{-}C_6)$alkyl or $-C(O)OR^5$. In at least one aspect, $X_n$ represents $(C_1\text{-}C_6)$alkyl, Y represents $(C_1\text{-}C_{30})$alkyl, wherein $(C_1\text{-}C_{30})$alkyl is substituted with 0-1 occurrences of $R^4$ and $R^4$ is $(C_1\text{-}C_6)$alkyl. In at least one aspect, $X_n$ represents $(C_1\text{-}C_6)$alkyl. In certain aspects, $X_n$ represents $(C_1\text{-}C_6)$alkyl, and Y represents $(C_1\text{-}C_{30})$alkyl, wherein $(C_1\text{-}C_{30})$alkyl is substituted with zero occurrences of $R^4$. In some aspects, $X_n$ is $CH_3$ and n is 3. In a further aspect, Y represents $-CH_2(CH_2)_{11}CH_3$ and n is substituted in the 2,4,6-positions. In a further aspect, Y represents $-CH_2C(CH_3)_3$ and n is substituted in the 2,4,6-positions. In certain aspects, $(C_1\text{-}C_{30})$alkyl is substituted with 1 occurrence of $R^4$ and $R^4$ is $-C(O)OR^5$. In at least one embodiment, n is substituted in the 2,4,6-positions, Y represents $-CH_2(CH_2)_7R^4$, and $R^4$ is $-C(O)OR^5$.

In one or more embodiments, Y represents $NR^aR^b$, and $R^a$ and $R^b$ represent $(C_1\text{-}C_6)$alkyl or aryl. In at least one embodiment, $R^a$ and $R^b$ represent $(C_1\text{-}C_6)$alkyl. In certain aspects, $X_n$ is $CH_3$ and n is 3. In a further embodiment, $R^a$ and $R^b$ are $CH_3$ and n is substituted in the 2,4,6-positions. In certain aspects, $X_n$ is $CH_3$ and n is 3. In a further embodiment, $R^a$ and $R^b$ represent an aryl. In yet a further embodiment, $R^a$ and $R^b$ are $C_6H_5$ and n is substituted in the 2,4,6-positions.

BRIEF DESCRIPTION OF THE DRAWINGS

Non-limiting embodiments of the systems and methods described herein will be conveyed by way of example, and optionally, with reference to the accompanying figures. In the following description, various embodiments of the systems and methods recited herein are described with reference to the following figures, in which.

DETAILED DESCRIPTION

Figure 1:
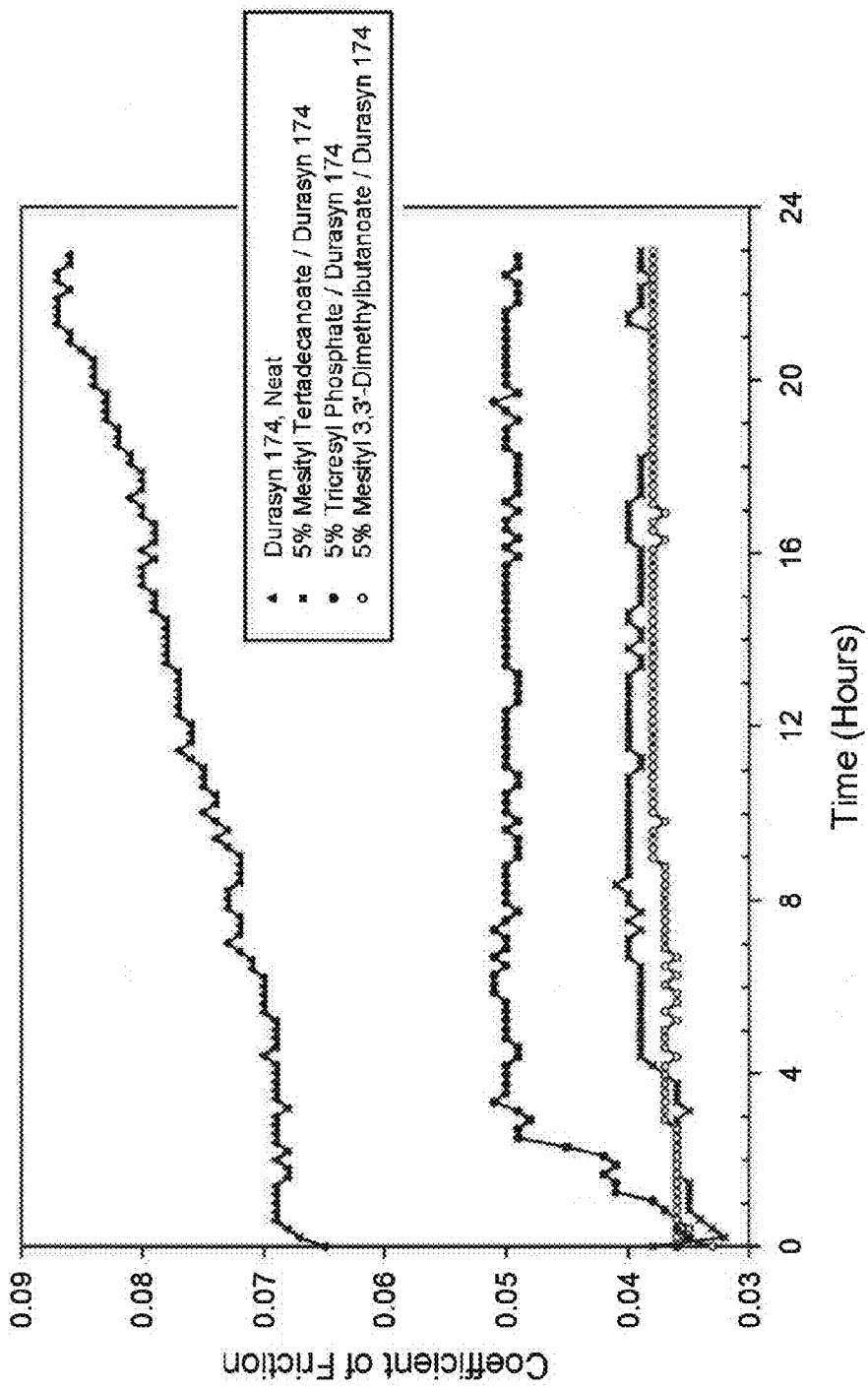
FIG. 1 is a graphic illustration of the results of tests performed in accordance with aspects of the present disclosure.

In certain aspects, one or more of the compounds disclosed herein may possess at least one of improved anti-wear and friction reducing properties, whether used alone, when combined with one or more other compounds, when incorporated into one or more other materials, such as a carrier, or any combination thereof. As used herein, the term "improved," when used in reference to the compounds or compositions disclosed herein, may refer to any improvement in a property or characteristic of the disclosed compound or composition as compared to the same property or characteristic of a conventional lubricant compound or composition. A conventional lubricant compound or composition may refer to any lubricant compound or composition known in the art. As used herein, the terms "friction reducing," "reducing a coefficient of friction," and "reduced mechanical friction" are used interchangeably. Unless stated otherwise, as used herein, the terms "reduced" or "reducing," or "reduction," when used in reference to the compounds or compositions comprising at least one compound disclosed herein, may refer to any reduction in a property or characteristic of the disclosed compound as compared to the same property or characteristic of a conventional lubricant compound, or as compared to the same property or characteristic of a composition without the at least one compound disclosed herein. The terms "coefficient of friction," "friction," or "mechanical friction," being either static or kinetic, generally refer to a measure of the sliding resistance of a material over another material. In certain aspects, the source of friction may be from sliding, rolling, starting, stopping, shock loading and the like, or combinations thereof. As used herein, the terms "improved anti-wear," "reducing wear," "reducing a rate of wear," "wear rate reduction," "improving wear protection," "increasing anti-wear properties," and "increased wear resistance" may be used interchangeably. These terms generally refer to a reduction in wear that is measureable in a properly designed wear test device, such as in a tribosystem. The generation of heat and wear are both associated with friction. In certain aspects, one or more compounds disclosed herein may reduce at least one of heat, wear, and friction when applied to one or more surfaces.

In certain aspects, one or more of the compounds disclosed herein may possess improved performance characteristics, whether used alone, combined with at least one other compound, combined with one or more other materials, such as a carrier, or any combination thereof. For example, the compound may possess one or more of improved solubility, stability, corrosion resistance, oxidative resistance, vapor pressure, surface tension, density, Newtonian behavior, viscosity, viscosity-temperature variation, and improved properties under extreme pressure conditions. According to further aspects, the compound may possess favorable electrostatic potential. In various aspects, the compound may possess a low vapor pressure.

As used herein, the term "stability" may refer to at least one of hydrolytic or thermal stability. The term "hydrolytic stability" refers to the ability of a material to retain its mechanical and chemical properties under exposure to elevated or predetermined temperatures and humidity for an extended period of time. The term "thermal stability" refers to the ability of a material to retain its mechanical and chemical properties under exposure to elevated or predetermined temperatures for an extended period of time. In certain aspects, stability may refer to the ability of a material to resist vaporization. In certain other aspects, stability may refer to the ability of a material to not separate. As used herein, the term "separate" generally refers to a composition that was uniform when prepared, but subsequently forms into distinct components, for example, individual components of differing density or viscosity.

In at least one aspect, one or more of the compounds disclosed herein may comprise a thixotropic paste. In certain aspects, the paste may be used alone or combined with other additives to form a lubricant composition. In various aspects, the paste may be used as a grease. In other aspects the paste may be combined with other additives that are not carriers, such as antioxidants, surfactants, and thermal stabilizers.

In various aspects, one or more of the compounds disclosed herein may be capable of interacting with at least one surface. The compounds may interact with the surface, for example, through one or more intermolecular forces. This type of interaction with the surface may provide an advantage over compounds or compositions that do not have this type of interaction. For example, tricresyl phosphate (TCP) and other phosphorous bearing compounds may directly and physically bind to the surface they come into contact with, making it difficult for the molecules of the compound to interchange with each other. As these compounds decompose over time, this inability to interchange causes the compounds to lose their functional lubricating properties at a faster rate than compounds that form non-covalent bonding with the surface, such as the compounds disclosed herein.

Other potential disadvantages of certain compounds, including phosphorus-containing compounds such as TCP, may be that they are not appreciably soluble in many carriers, such as hydrocarbons. In addition, their breakdown products or by-products may fail to emit strong, identifiable signatures. This may make them difficult to identify with chemical analysis. In another aspect, these compounds may contain phosphorous or other inorganic compounds that may be considered to be hazardous to the environment.

At least one of the disclosed compounds and compositions may provide at least partial protection to one or more surfaces. In certain embodiments, at least one of the disclosed compounds and compositions may provide complete protection to one or more surfaces. The compounds and compositions may comprise one or more characteristics, such as being longer lasting, safer to handle, able to reduce waste disposal problems, and able to provide longer lasting protection over conventional lubricant compounds and compositions. The disclosed compounds and compositions may contain little or no phosphorus or other similar inorganic compounds that may be considered harmful to the environment. They may also function to improve fuel economy, increase horsepower and torque, and prevent damage from total loss of lubricant as compared to conventional lubricant compounds and compositions. The disclosed compounds and compositions may also further eliminate excessive wear from dry starts, protect equipment from contamination, reduce heat due to friction, and reduce wear. These benefits may result in lower maintenance costs, extended equipment life cycles, and reduced levels of environmentally harmful emissions.

The disclosed compounds may function to allow the lubricant composition to remain on one or more surfaces, even under one or more conditions of extreme pressure, low speeds, high speeds, and high temperatures. The disclosed compounds may reduce friction and wear between rotating and sliding surfaces in extreme environments. These reductions may reduce preventative maintenance costs by increasing efficiency and reducing downtime, which in turn, may maximize energy generation and profits.

In certain aspects, the disclosed compounds may be custom-tailored for one or more specific applications or uses. For example, the compounds may be tailored to be made adaptable to a particular substrate or temperature profile. This may be an additional advantage over certain other compounds, including phosphorous-containing compounds, which may not offer as wide a range of tailorable flexibility. In various aspects, the disclosed compounds may be tailored based on a desired electrostatic potential. In one or more aspects, the compounds may be tailored based on minimizing one or more molecular energy differences using molecular mechanics calculations.

In accordance with one or more embodiments, the compounds, compositions, and methods disclosed herein related to a compound comprising the formula (I):

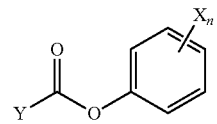

$X_n$ may include any suitable functional group or moiety capable of providing or enhancing desired properties of one or more of the compounds disclosed herein. In certain aspects, $X_n$ may be selected such that when the compound is used alone, $X_n$ is capable of forming a compound, and when the compound is combined with one or more other substances, $X_n$ may function to enhance the solubility of the compound in the one or more other substances. According to one or more other aspects, $X_n$ may be selected to provide the compound with one or more improved performance characteristics, for example, corrosion resistance, oxidative resistance, vapor pressure, surface tension, density, Newtonian behavior, viscosity, viscosity-temperature variation, and improved properties under extreme pressure conditions. According to further aspects, $X_n$ may be selected to provide the compound with more favorable electrostatic potential. $X_n$ may be selected to provide the above-mentioned performance characteristics of the compound when used in combination with one or more other compounds, when used with one or more other compositions, or both. In at least one aspect, $X_n$ may be selected such that when the compound is provided to at least one surface, the compound reduces mechanical friction of the at least one surface. In certain aspects, $X_n$ may be selected such that when the compound is provided to at least one surface, the compound increases wear resistance of the at least one surface. In one or more aspects, $X_n$ may be selected such that when the compound is provided to at least one surface, the compound reduces mechanical friction and increases wear resistance of the at least one surface.

In certain aspects, $X_n$ may be selected to promote the capability of the compound in interacting with at least one surface through one or more intermolecular forces. As used herein, the term "intermolecular force" refers to non-covalent types of interactions. For example, the compound may interact with at least one surface through at least one of an electrostatic bond, a van-der-Waals force, a dipole-dipole interaction, and a reversible covalent bond.

In one or more embodiments, $X_n$ may be selected from alkyl or alkoxy. As used herein, the term "alkyl" refers to any functional group or substituent derived from single-bonded carbon and hydrogen atoms. As used herein, the term "alkoxy" refers to any functional group or substituent derived from an alkyl that is single-bonded to oxygen. The alkyl and alkoxy may be straight, branched, or cyclic. $X_n$ may be selected to impart particular properties to the compound. For example, the number of carbon atoms in the alkyl or alkoxy may be selected to promote solubility of the compound in a carrier, or to promote stability of the compound, or both. In certain embodiments, the alkyl or alkoxy may comprise between one and ten carbon atoms. In certain other embodiments, the alkyl or alkoxy may comprise between one and six carbon atoms. In some embodiments, the alkyl or alkoxy may comprise between one and three carbon atoms. In at least one embodiment, the alkyl may represent one carbon atom, methyl.

In certain embodiments, $X_n$ may be a heteroatom. The heteroatom may be selected to enhance the ability of the compound in coordinating with one or more surfaces. As used herein, the term "heteroatom" refers to any atom other than carbon or hydrogen. Non-limiting examples of heteroatoms include, for example, oxygen (O), sulfur (S), nitrogen (N), phosphorus (P), boron (B), silicon (Si), and halogens, including fluorine (F), chlorine (Cl), bromine (Br), and iodine (I). In certain embodiments, the heteroatom may include phosphorus (P), sulfur (S), or a halogen. As used herein, the term "halogen" refers to nonmetal elements of Group VIIA of the periodic table. Non-limiting examples of halogens include fluorine (F), chlorine (Cl), bromine (Br), and iodine (I).

In accordance with one or more embodiments, n may be any value that is suitable for the purposes and features of the compound as described above. For example, n may be a value that enhances the solubility of one or more compounds or compositions disclosed herein. In at least one embodiment, n may be zero to five. In some embodiments, n may be one to five. In certain embodiments, n may be three to five. In another embodiment, n may be three. When n is greater than one, $X_n$ may be selected individually or independently from one another. Likewise, when n is greater than one, $X_n$ may be selected to be the same functional group or moiety. In various aspects, n may be substituted in at least one of the second, third, fourth, fifth, or sixth positions. For example, n may be substituted in the 1,3-, 1,4-, 1,2,3-, 2,4,6-positions, or may be singularly substituted in the 2-position. The positioning of n may be selected to provide or enhance one or more desired characteristics of the lubricant compound. In at least one embodiment, $X_n$ may represent $(C_1-C_6)$alkyl, $(C_1-C_6)$alkoxy, or heteroatom, and n may be zero to five. In certain embodiments, $X_n$ may represent $(C_1-C_6)$alkyl. In certain other embodiments, $X_n$ may be $CH_3$ and n may be three. In certain embodiments, n may be substituted in the 2,4,6-positions. According to one or more aspects, $X_n$ may be selected from the group consisting of alkyl, alkoxy, and heteroatom, and n may be zero to five.

Y may include any suitable functional group or moiety capable of providing or enhancing desired properties of one or more of the compounds disclosed herein. Y may be selected to impart particular properties to the compound. For example, Y may be selected to promote solubility of the compound, to promote stability of the compound, or both. In certain aspects, Y may be selected such that when the compound is used alone, it may be capable of forming a compound or finished product. When the compound is combined with one or more other substances, it may function to enhance the solubility of the compound in the one or more other substances. According to one or more other aspects, Y may be selected to provide the compound with one or more improved performance characteristics such as corrosion resistance, oxidative resistance, vapor pressure, surface tension, density, Newtonian behavior, viscosity, viscosity-temperature variation, and improved properties under extreme pressure conditions. According to further aspects, Y may be selected to provide the compound with more favorable electrostatic potential. Y may be selected to provide the above-mentioned performance characteristics of the compound when used alone, when used in combination with one or more other compounds, or when used in combination with one or more other substances, such as a carrier. In certain aspects, Y may be selected to promote the capability of the compound to interact with at least one surface through one or more intermolecular forces. In at least one aspect, Y may be selected such that when the compound is provided to at least one surface, the compound reduces mechanical friction of the at least one surface. In certain aspects, Y may be selected such that when the compound is provided to at least one surface, the compound increases wear resistance of the at least one surface. In one or more aspects, Y may be selected such that when the compound is provided to at least one surface, the compound may reduce mechanical friction and may increase wear resistance of the at least one surface.

In various embodiments, Y may be an alkyl, as described and characterized above. In some embodiments, the alkyl may comprise between one and 30 carbon atoms. In certain embodiments, the alkyl may comprise between one and 25 carbon atoms. In other embodiments, the alkyl may comprise between one and 15 carbon atoms. In various embodiments, the alkyl may comprise between three and 15 carbon atoms. Examples of alkyl include, but are not limited to, methyl, ethyl, n-propyl, i-propyl, n-butyl, i-butyl, and t-butyl. In at least one embodiment, the alkyl may represent $—CH_2(CH_2)_{11}CH_3$. In at least one other embodiment, the alkyl may represent $—CH_2C(CH_3)_3$.

In accordance with certain aspects, Y may be an aryl. The term "aryl" refers to any functional group or substituent derived from an aromatic ring. In certain embodiments, the aryl may include aromatic monocyclic or polycyclic ring systems, such as tricyclic or bicyclic ring systems. The aryl may include fused ring systems wherein at least two aryl rings share at least one chemical bond. The aromatic ring may comprise between six and 12 carbon atoms, and may comprise more than one ring, for example, between two and four rings. Non-limiting examples of aryl include phenyl, naphthyl, thienyl, inodyl, tolyl, xylyl, anthryl, and phenanthryl. In at least one embodiment, the aryl may represent $C_6H_5$ (phenyl).

In certain aspects, Y may be a heteroaryl. The term "heteroaryl" refers to any functional group or substituent derived from an aromatic ring comprising carbon atoms, hydrogen atoms, and one or more heteroatoms, such as oxygen (O), nitrogen (N), sulfur, (S), phosphorus (P), or selenium (Se). The aromatic ring may comprise between five and 12 carbon atoms, and may include five-membered or six-membered heterocyclic rings, polycyclic heteroaromatic ring systems, or polyheteroaromatic systems, where the ring system comprises two, three, or four rings. Non-limiting examples of a heteroaryl include pyridyl, furyl, imidazolyl, benzimidazolyl, pyrimidinyl, thienyl, quinolinyl, indolyl, thiazolyl, pyrrolyl, isoquinolinyl, purinyl, oxazolyl, pyrazolyl, and carbazolyl.

In various embodiments, Y may be an amine. The term "amine" refers to any functional group or substituent where a nitrogen atom is covalently bonded to at least one carbon, hydrogen, or heteroatom. The amine may be acyclic, cyclic, saturated, unsaturated, branched, unbranched, and may comprise more than one nitrogen atom. Non-limiting examples of amine include compounds represented by the formulas $NH_2$, $NHR^a$, and $NR^aR^b$. In certain embodiments, $R^a$ and $R^b$ may be alkyl, alkoxy, aryl or heteroaryl, as described above. In at least one embodiment, $R^a$ and $R^b$ may represent methyl. In at least one other embodiment, $R^a$ and $R^b$ may represent $C_6H_5$ (phenyl).

In certain aspects, Y may be a heteroatom, as described and referenced above. For example, the heteroatom may include phosphorus (P), sulfur (S), or a halogen. The heteroatom may be selected to provide or enhance one or more desired characteristics of the lubricant compound.

In some embodiments, the alkyl, aryl, heteroaryl, and amine discussed above in reference to Y may be substituted with one or more substituents. In certain embodiments, the alkyl, aryl, heteroaryl, and amine may comprise between one and five substituents. In certain other embodiments, the alkyl, aryl, heteroaryl, and amine may comprise between one and three substituents. The substituents may be selected from alkyl, alkoxy, ester, aryl and heteroaryl. The alkyl, alkoxy, aryl, and heteroaryl may be provided as discussed and described above. In certain aspects, the substituent alkyl and alkoxy may comprise between one and 18 carbon atoms. In certain other aspects, the substituent alkyl and alkoxy may comprise between one and 10 carbon atoms. In at least one embodiment, the substituent alkyl and alkoxy may comprise between one and six carbon atoms.

In various embodiments, the substituent may be an ester. The term "ester" refers to any functional group or substituent having a carbonyl group (C=O) linked to an alkoxy group. The ester may be unbranched, branched, saturated, or unsaturated. In at least one embodiment, the ester may represent —$C(O)OR^5$. In certain embodiments, $R^5$ may be selected from alkyl, aryl, and heteroaryl, as described and characterized above. In at least one embodiment, $R^5$ may represent 2,4,6-trimethylphenyl.

In at least one embodiment, Y may represent $(C_1-C_{30})$ alkyl, aryl, heteroaryl, $NR^aR^b$, or heteroatom, wherein $(C_1-C_{30})$alkyl, aryl, and heteroaryl may be substituted with zero to three occurrences of $R^4$, $R^a$ and $R^b$ may represent $(C_1-C_6)$ alkyl, $(C_1-C_6)$alkoxy, aryl, or heteroaryl, $R^4$ may represent $(C_1-C_6)$alkyl, $(C_1-C_6)$alkoxy, —$C(O)OR^5$, aryl, or heteroaryl, and $R^5$ may represent 2,4,6-trimethylphenyl. In certain other aspects, Y may represent $(C_1-C_{30})$alkyl or $NR^aR^b$, wherein $(C_1-C_{30})$alkyl may be substituted with zero to one occurrences of $R^4$, $R^4$ may represent $(C_1-C_6)$alkyl, $(C_1-C_6)$alkoxy, or —$C(O)OR^5$, and $R^5$ may represent 2,4,6-trimethylphenyl. In various aspects, Y may represent $(C_1-C_{30})$alkyl, wherein $(C_1-C_{30})$alkyl may be substituted with zero to one occurrences of $R^4$; $R^4$ may represent $(C_1-C_6)$alkyl or —$C(O)OR^5$, and $R^5$ may represent 2,4,6-trimethylphenyl. In one or more aspects, Y may represent $(C_1-C_{30})$alkyl, wherein $(C_1-C_{30})$alkyl may be substituted with zero to one occurrences of $R^4$ and $R^4$ may be $(C_1-C_6)$alkyl. In at least one aspect, $(C_1-C_{30})$alkyl may be substituted with zero occurrences of $R^4$. In another aspect, Y may represent —$CH_2(CH_2)_{11}CH_3$. In yet another aspect, $(C_1-C_{30})$alkyl may be substituted with one occurrence of $R^4$, $R^4$ may represent —$C(O)OR^5$, and $R^5$ may represent 2,4,6-trimethylphenyl. According to another aspect, Y may represent —$CH_2(CH_2)_7R^4$, $R^4$ may represent —$C(O)OR^5$, and $R^5$ may represent 2,4,6-trimethylphenyl. In certain aspects, Y may represent $NR^aR^b$, and $R^a$ and $R^b$ may represent $(C_1-C_6)$alkyl or aryl. In at least one aspect, $R^a$ and $R^b$ may represent $(C_1-C_6)$alkyl. In at least another aspect, $R^a$ and $R^b$ may represent $CH_3$. In various aspects, $R^a$ and $R^b$ may represent an aryl. In certain aspects, $R^a$ and $R^b$ may represent $C_6H_5$. According to one or more other aspects, Y may be selected from the group consisting of alkyl, aryl, heteroaryl, amine, and heteroatom. According to a further aspect, Y may be substituted with zero to three occurrences of $R^4$, and $R^4$ may be selected from the group consisting of alkyl, alkoxy, ester, aryl, and heteroaryl.

In at least one embodiment the compound may comprise:

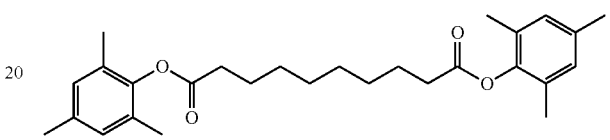

which may be referred to as 1,10-dimesityl sebacylate or dimesityl decanedioate.

In accordance with one or more embodiments, the compound may comprise:

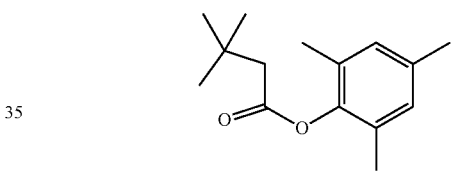

which may be referred to as mesityl 3,3-dimethylbutanoate.

In various embodiments, the compound may comprise:

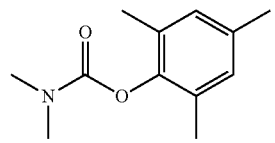

which may be referred to as mesityl dimethylcarbamate.

In certain embodiments, the compound may comprise:

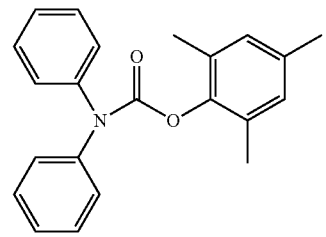 [SMILES: Cc1cc(C)c(OC(=O)N(c2ccccc2)c2ccccc2)c(C)c1]

which may be referred to as mesityl diphenylcarbamate.

In certain embodiments, the compound may comprise:

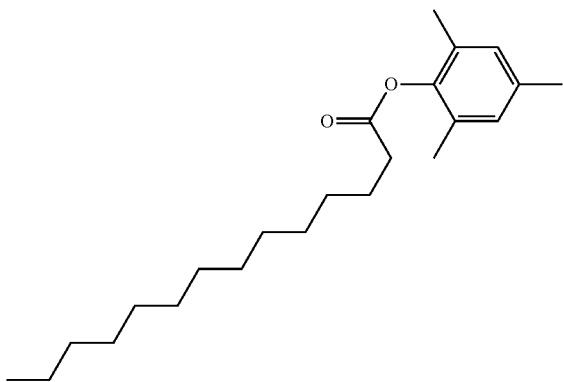 [SMILES: CCCCCCCCCCCCCC(=O)Oc1c(C)cc(C)cc1C]

which may be referred to as mesityl tetradecanoate.

In accordance with one or more embodiments, the systems and methods disclosed herein may provide a lubricant composition. In certain embodiments, the lubricant composition may comprise one or more of the compounds disclosed herein. In accordance with certain embodiments, when the lubricant composition is provided to at least one surface, the lubricant composition may reduce the coefficient of friction of the at least one surface. In accordance with other embodiments, when the lubricant composition is provided to at least one surface, the lubricant composition may reduce wear of the at least one surface. In certain embodiments, when the lubricant composition is provided to at least one surface, the lubricant composition may reduce the coefficient of friction and reduce wear of the at least one surface. In various aspects, the lubricant composition may reduce friction of at least one surface, which may create a corresponding or greater reduction in consumption of energy. In certain embodiments, the lubricant composition comprising one or more of the compounds may exhibit improved stability and compatibility when used in the presence of one or more other additives in the lubricant composition. In certain aspects, the lubricant composition may reduce at least one of heat, wear, and friction when applied to at least one surface.

In certain aspects, the lubricant composition may possess improved performance characteristics when used with one or more of the compounds disclosed herein. For example, the lubricant composition may possess one or more of improved solubility, stability, such as thermal stability, corrosion resistance, oxidative resistance, vapor pressure, surface tension, density, Newtonian behavior, viscosity, viscosity-temperature variation, and improved properties under extreme pressure conditions. According to further aspects, the lubricant composition may possess more favorable electrostatic potential. In at least one aspect, the lubricant composition may possess a low vapor pressure. In various aspects, the lubricant composition disclosed herein may be capable of interacting with at least one surface through one or more intermolecular forces. According to one or more aspects, the compounds, compositions, methods, and systems disclosed herein may provide for one or more increased performance characteristics under one or more operating environmental conditions. In certain aspects, the operating environmental condition may be deemed extreme in terms of at least one of temperature, pressure, humidity, force, vibration, electromagnetic, or otherwise. In various aspects, the compounds and compositions may provide for one or more increases in performance characteristics under a wide variety of environments, including conditions experienced in drilling or mining, manufacturing, commercial or military aerospace, other military applications, and automotive, rail, and mass transit applications. In certain aspects, the environmental condition may be described as highly corrosive, such as in an ocean environment.

In accordance with one or more aspects, the compounds and compositions disclosed herein may decompose into non-toxic breakdown products or by-products. According to certain aspects, the compounds and compositions disclosed herein may be inexpensive to manufacture. In addition, the compounds and compositions may be manufactured in mass quantities, and may be suitable for use in the automotive, manufacturing, aerospace industries, and alternative energy industries, for example energy industries based on wind, water, and solar technologies.

The compounds and compositions disclosed herein may be applied to a multiplicity of fields and uses. In general, compounds and compositions disclosed herein may be used in any field for any task requiring a compound or composition providing at least one of reduced mechanical friction reduction and increased wear resistance. In accordance with certain aspects, the compounds and compositions disclosed herein may be useful in industrial, commercial, and residential applications. For example, the compounds and compositions may be used in one or more components of an automobile or truck, such as the engine, transmission, bearings, drive shafts, and axles. In addition, the compounds and compositions may be used in two-cycle engines, aviation piston engines, natural gas engines, stationary power engines, turbines, marine and low-load diesel engines, and the like. In various aspects, the compounds and compositions may be used in railroads and other rail systems. In certain aspects, automatic or manual transmission fluids, farm tractor fluids, transaxle lubricants, gear lubricants, metal-working lubricants, hydraulic fluids, and other lubricating oil and grease compositions can benefit from the incorporation of the compounds and compositions disclosed herein. They may also be used for wireropes, walking cams, slideways, rock drills, chain and conveyor belts, worm gears, bearings, and rail and flange applications. In the area of machining, the compounds and compositions disclosed herein may be used for cutting, drilling, compressing, and extruding.

In accordance with one or more embodiments, the compounds, compositions, methods and systems disclosed herein may be directed toward a coating. The coating may functionally passivate or protect one or more surfaces subject to at least one or more external forces, for example those related to frictional or corrosive forces. As used herein, the term "passivate," means to make inactive or less reactive. In certain instances, passivate may mean to protect against contamination by coating or surface treating. One or more coatings may be provided by using conventional coating application procedures, such as spraying, brushing, or rolling the coating onto one or more surfaces requiring protection.

In various embodiments, the lubricant composition may comprise at least one compound represented by the above-described formula (I) and each of the groups Y and $X_n$ may be independently configured as set forth in the previous sections to the extent that they are consistent with the above descriptions and definitions.

In accordance with one or more embodiments, the lubricant composition may comprise at least one carrier. The carrier may include any carrier suitable for the purposes of performing as a carrier, provided the carrier does deter from desired properties of the compounds and compositions disclosed herein. In some aspects, the carrier may be, for example, an oil. The oil may be based on a mineral oil or a synthetic oil. As used herein, the term "oil" refers to a liquid component mainly consisting of hydrophobic compounds. In other aspects, the carrier may be characterized as paraffinic, naphthenic, aromatic, and mixtures thereof. The carrier may comprise polyalkylene glycols (PAG), polyisobutylene (PIB), phosphate esters, diesters, polyol esters, natural esters, or any combination thereof. In certain aspects, the carrier may comprise solid lubricants. Non-limiting examples include graphite, molybdenum disulfide, boron nitride, tetrafluoroethylene (TEFLON® material), and combinations thereof.

In certain aspects, the carrier may be a grease. The term "grease," as used herein, refers to any type of oil, fat, or lipid, whether natural or synthetic, and includes without limitation, natural fats and oils, such as seed oils, including corn oil, soybean oil, rapeseed oil, sunflower oil, and the like, lard, animal fats, and synthetic oils, such as silicone oil and the like, and also liquid, semi-solid and solid hydrocarbons. In certain aspects, grease may refer to a thick oil or viscous substance. In other aspects, grease may refer to a composition comprising at least 30 carbon atoms. In certain aspects, grease may refer to a composition that is organic or inorganic, substantially water-insoluble, and semi-solid at room temperature. In one or more instances, the grease may be used as gear grease. Other classes of greases may include greases for automobile chassis lubrication, greases for journal and wheel bearings, and the like. The range of applications may include the automotive, railway, and aviation industries, and alternative energy systems, for example energy systems based on wind, wave, and solar technologies.

In certain embodiments, the carrier may be present in the lubricant composition by an amount that provides the desired properties to create a suitable lubricant for its intended purpose. An effective amount, for example, would be a weight percent that is sufficient to impart one or more desired properties to the lubricant composition, given the characteristics of the compound, the characteristics of the carrier, the specific application for the composition, and the conditions for use. In certain embodiments, an effective amount of carrier would be a weight percent that is sufficient to impart one or more desired properties to the lubricant composition given the characteristics of the at least one compound, the carrier, the specific application for the composition, and the conditions for use, while not imparting undesired or reducing one or more desired properties of the lubricant composition. For example, the carrier may be present in the lubricant composition by an amount less than about 10% by weight. In another example, the carrier may be present in an amount less than about 20% by weight. In certain embodiments, the lubricant composition may not comprise a carrier material. In other examples, the carrier may be present in the lubricant composition by an amount greater than about 50% by weight. In certain embodiments, the carrier may be present in an amount greater than about 10%, greater than about 20%, greater than about 30%, greater than about 40%, greater than about 50%, greater than about 60%, greater than about 70%, greater than about 80%, greater than about 90%, or greater than about 95% by weight of the lubricant composition. In various embodiments, the concentration of carrier in the lubricant composition may range from about 95% to about 99.5%. The percent of carrier by weight of the lubricant composition may be any percentage or range in between about 0% and about 99.5%. As used herein, the word "about" is used to account for variance in measurement due to inherent errors associated with measurement techniques. The word "about," even if not explicitly used, is understood to modify all measurements disclosed, unless otherwise stated.

In certain aspects, the carrier may comprise at least one hydrocarbon. The hydrocarbon may be selected to provide the lubricant composition with desired properties, such as those discussed above. As used herein, the term "hydrocarbon" refers to organic material with molecular structures containing carbon bonded to hydrogen. Hydrocarbons may also include other elements, such as, but not limited to, at least one of halogens, metallic elements, nitrogen, oxygen, and sulfur. Non-limiting examples of hydrocarbon liquids include polyalphaolefins, polydecene based oils, and mineral oils.

In certain embodiments, the hydrocarbon may comprise one or more aliphatic groups, for example alkyl or alkenyl, alicyclic, (including cycloalkyl or cycloalkenyl), aromatic, aliphatic- and alicyclic-substituted aromatic, aromatic-substituted aliphatic and alicyclic groups, and the like, as well as cyclic groups wherein the ring is completed through another portion of the molecule, for example, where any two indicated substituents may together form an alicyclic group. Non-limiting examples include methyl, ethyl, octyl, decyl, octadecyl, cyclohexyl, phenyl, and any combination thereof.

In another aspect, the hydrocarbon may comprise substituted hydrocarbon groups, where groups containing non-hydrocarbon substituents which, in the context of the compositions and methods disclosed herein, do not alter the predominantly hydrocarbon character of the group. Non-limiting examples include halo, hydroxy, nitro, cyano, alkoxy, acyl, and any combination thereof.

In certain aspects, the hydrocarbon may comprise one or more hydrocarbon-based oils. Non-limiting examples include mineral oils, highly refined mineral oils, and synthetic oils. Examples of synthetic oils may include, but are not limited to, polyalphaolefins, polyalkylene glycols, polyisobutylenes, phosphate esters, silicone oils, diesters, polyol esters, and other synthetic esters.

In certain aspects, the carrier may comprise one or more oils. The oils may be unrefined, refined, or re-refined oils, either natural or synthetic, or any combination thereof. As used herein, unrefined oils are those obtained directly from a natural or synthetic source without further purification treatment. For example, a petroleum oil obtained directly from a primary distillation operation, or an ester oil obtained directly from an esterification process and used without further treatment, would all be non-limiting examples of unrefined oil. As used herein, refined oils are similar to unrefined oils, with the distinction that they have been further treated by one or more purification steps to improve one or more chemical or physical properties. Non-limiting examples of purification techniques include solvent extraction, secondary distillation, acid or base extraction, filtration, percolation, and the like. As used herein, re-refined oils (also known as reclaimed or reprocessed oils) are obtained by processes similar to those used to obtain refined oils, with the distinction that these processes are applied to refined oils that have already been used in service. The re-refined oils may be processed by techniques directed to remove spent additives and oil breakdown products.

In various embodiments, the carrier may comprise one or more synthetic oils. The term "synthetic oil" refers to chemically synthesized oils. Synthetic oils may include hydrocarbon oils such as polymerized and interpolymerized olefins (for example polybutylenes, polypropylenes, and propylene-isobutylene copolymers), including, for example, polyalphaolefins. Synthetic oils may include halo-substituted hydrocarbon oils, hydrogenated synthetic oils, alkylene oxide polymers, alkylated aromatics, such as alkylated naphthalenes, aliphatic or aromatic carboxylic acid esters, polymeric esters, alkylbenzenes, such as dodecylbenzenes, tetradecylbenzenes, dinonylbenzenes, di-(2-ethylhexyl)benzenes, and the like, trimethylol propane esters, neopentyl and pentaerythritol esters, polyalkylene oxides, phosphoric acid esters, silicate esters, silanes, siloxanes, silicones (polysiloxanes), polyphenyls such as biphenyls, terphenyls, alkylated polyphenyls, and the like, glycols, polyglycols, polyethylene glycol, polypropylene glycol, polyalkylene glycols, polymeric tetrahydrofurans, alkylated diphenyl ethers, alkylated diphenyl sulfides, the derivatives, analogs, and homologs thereof, and combinations of any of them. Synthetic oils may include long chain alkanes, for example, cetanes, and olefin polymers such as oligomers of hexene, octene, decene, and dodecene, and any combination thereof.

In certain instances, the synthetic oil may be a silicon-based oil. Non-limiting examples of silicon-based oils include polyalkyl-, polyaryl-, polyalkoxy-, or polyaryloxy-siloxane oils. Silicon-based oils may include silicate oils, for example, tetraethyl silicate, tetraisopropyl silicate, tetra-(2-ethylhexyl)silicate, tetra-(4-methylhexyl)silicate, tetra-(p-tert-butylphenyl) silicate, hexyl-(4-methyl-2-pentoxy)disiloxane, poly(methyl)siloxanes, poly-(methylphenyl) siloxanes, and the like.

In certain embodiments, the carrier may comprise at least one polyalphaolefin (PAO). The polyalphaolefin may be derived from monomers having between three to 30 carbon atoms, between four to 20 carbon atoms, or between six to 16 carbon atoms. Non-limiting examples of PAOs include those derived from decene. These PAOs may have a viscosity from about three to about 150, or from about four to about 100, or from about four to about eight centiStokes (cSt) at 100° C. Examples of PAOs include four cSt polyolefins, six cSt polyolefins, 40 cSt polyolefins and 100 cSt polyalphaolefins.

In certain instances, the carrier may comprise one or more DURASYN® polyalphaolefin lubricants (INEOS Oligomers, League City, Tex.). DURASYN® lubricants are synthetically produced from linear 1-decene and may be both thermally stable and resistant to oxidative degradation. In various aspects, the carrier may comprise a DURASYN® 174 lubricant.

According to another aspect, the carrier may comprise one or more fluorocarbon-based lubricants, such as KRYTOX® lubricants (Dupont, Wilmington, Del.). KRYTOX® lubricants are available in a variety of formulas, including oils and greases.

In accordance with certain embodiments, the carrier may comprise one or more natural oils. Examples of natural oils may include, but are not limited to, animal oils, vegetable oils (castor oil, lard oil), rapeseed oils, canola oils and sunflower oils, mineral oils such as liquid petroleum oils, and solvent treated or acid-treated mineral lubricating oils of the paraffinic, naphthenic or mixed paraffinic-naphthenic types.

In certain aspects, the carrier may comprise a polymeric resin. As used herein, the term "polymeric resin" refers to class of polymers that soften or become liquid when heated and harden when cooled. Non-limiting examples include acrylics, urethanes, epoxies, vinyl acrylics, styrene butadienes, ureas, polyurea, silicones, and silicates.

In at least one aspect, the carrier may comprise polyethylene glycol (PEG). As used herein, PEG refers to an oligomer or polymer of ethylene oxide. The PEG may be branched, having between three and ten PEG chains emanating from a central core group. The PEG may be star-shaped, having between ten and 100 PEG chains emanating from a central core group. The PEG may be comb-shaped, having multiple PEG chains normally grafted to a polymer backbone. The PEG may also include any combination of these geometries.

In certain aspects, one or more of the compounds disclosed herein may be at least partially soluble in PEG.

In certain aspects, the carrier may comprise one or more ionic liquids. As used herein, the term "ionic liquid" refers to any organic salt that is a liquid at a temperature at or below about 25° C. (room temperature). The ionic liquid may comprise anion and cation molecules. In certain aspects, the anion and cation molecules may be organic or inorganic. The ionic liquid may comprise ions and neutral molecules. Non-limiting examples of ionic molecules include imidazolium, phosphonium, and choline chloride. The ionic liquid may be thermally stable, especially at high operating temperatures. In various aspects, the ionic liquid may be combined or dissolved in one or more other carriers, such as a fluorocarbon-based carrier or a hydrocarbon carrier. In certain aspects, the ionic liquid may be used as an additive to the compositions disclosed herein. In certain aspects, one or more of the compounds disclosed herein may be at least partially soluble in one or more ionic liquids.

In certain embodiments, the compounds disclosed herein may be at least partially soluble in one or more of the previously characterized and discussed carriers. For example, in certain embodiments, one or more of the compounds disclosed herein may be at least partially soluble in at least one hydrocarbon. In various embodiments, one or more of the compounds may be completely soluble in at least one hydrocarbon. In one or more embodiments, one or more of the compounds may be at least partially soluble in at least one of a polar and a non-polar organic carrier. In one or more embodiments, the compounds may also be at least partially soluble in greases or other solid lubricants.

In accordance with the methods and systems disclosed herein, the lubricant composition may comprise one or more additives. In certain embodiments one or more additives may function to impart their customary properties to the composition, and may not detract from the functionality of the compositions and systems disclosed herein. In certain aspects, one or more additives may create or further enhance one or more of the properties of the compositions disclosed herein. Non-limiting examples of suitable additives may include antioxidants, anti-foaming agents, coupling agents, color stabilizers, corrosion inhibitors, defoamants, detergents, dispersants, diluents, extreme pressure agents, viscosity index improvers, demulsifiers, metal deactivators, pour-point depressants, seal compatibility additives, surfactants, thickeners, friction reducers, anti-wear agents and the like. In other aspects, one or more additives may be present at a sufficient concentration to provide the compositions with enhanced properties, which may depend upon the intended use. In some aspects, one or more additives may be used in an effective amount to impart one or more desired properties to the lubricant composition. For example, if an additive is a dispersant, an effective amount of this dispersant may be an amount sufficient to impart the desired dispersancy characteristics to the composition. An effective amount of additive, for example, would be a weight percent that is sufficient to impart one or more desired properties to the lubricant composition given the characteristics of the at least one compound, the characteristics of the carrier, the characteristics of the additive, the specific application for the composition, and the conditions for use. In certain embodiments, an effective amount of additive would be a weight percent that is sufficient to impart one or more desired properties to the lubricant composition given the characteristics of the additive, the specific application for the composition, and the conditions for use, while not imparting undesired characteristics or reducing one or more desired properties of the lubricant composition.

For example, in some embodiments, the lubricant composition may not comprise an additive. In other embodiments the composition may comprise less than about 2% additive. The concentration of one or more additives, when used, may range from about 0% to about 20%, from about 0% to about 10%, from about 0% to about 3%, from about 0% to about 1%, or from about 0% to about 0.5%, based on the total weight of the lubricant composition. The percent of additive by weight of the lubricant composition may be any percentage or range in between about 0% and about 20%.

In certain non-limiting embodiments, the lubricant composition may comprise one or more thickeners or gelling agents. Thickeners may include one or more metal salts or soaps, such as calcium, lithium stearates, and hydroxystearates. Other exemplary thickeners may include alkali and alkaline earth metal soaps of fatty acids and fatty materials having from about 12 to about 30 carbon atoms per molecule. Non-limiting examples of metals may include sodium, lithium, calcium and barium. Fatty materials may be exemplified by stearic acid, hydroxystearic acid, stearin, cottonseed oil acids, oleic acid, palmitic acid, myristic acid and hydrogenated fish oils. A non-limiting example of a thickener may include lithium stearate. Suitable thickeners may include salt and salt-soap complexes such as calcium stearate-acetate, barium stearate acetate, calcium stearate-caprylate-acetate complexes, calcium caprylate-acetate, and calcium salts and soaps of acids. Thickeners may comprise non-soap thickeners, including surface-modified clays and silicas, aryl ureas, calcium complexes, and the like. In certain embodiments, suitable thickeners are characterized in that they do not melt or dissolve when used at a certain temperature or under certain environmental conditions. Other suitable thickeners may include polyacrylates, polymethacrylates, vinylpyrrolidone/methacrylate copolymers, polyvinylpyrrolidones, polybutenes, olefin copolymers, styrene/acrylate copolymers, and polyethers.

In various embodiments, the lubricant composition may comprise at least one pressure agent, corrosion inhibitor, and antioxidant. Non-limiting examples may include chlorinated aliphatic hydrocarbons such as chlorinated wax; organic sulfides and polysulfides such as benzyl disulfide, bis(chlorobenzyl)disulfide, dibutyl tetrasulfide, sulfurized methyl ester of oleic acid, sulfurized alkylphenol, sulfurized dipentene, and sulfurized terpene; phosphosulfurized hydrocarbons such as the reaction product of a phosphorus sulfide with turpentine or methyl oleate; metal thiocarbamates, such as zinc dioctyldithiocarbamate, and barium heptylphenyldithiocarbamate; dithiocarbamate esters from the reaction product of dithiocarbamic acid and acrylic, methacrylic, maleic, fumaric or itaconic esters; dithiocarbamate containing amides prepared from dithiocarbamic acid and an acrylamide; alkylene-coupled dithiocarbamates; sulfur-coupled dithiocarbamates. Suitable antioxidants may include hindered phenols, for example Ethanox® 702 (Albemarle, Baton Rouge, La.).

In certain embodiments, the corrosion inhibitor or antioxidant may comprise organic acids and esters, metal salts and anhydrides thereof, for example N-oleylsarcosine, sorbitan monooleate, and lead naphthenate, alkenylsuccinic anhydrides, for example dodecenylsuccinic anhydride, partial esters and partial amides of alkenylsuccinic acids. In some embodiments, the corrosion inhibitor or antioxidant may comprise nitrogen-containing compounds, for example primary, secondary or tertiary aliphatic or cycloaliphatic amines and amine salts of organic and inorganic acids; heterocyclic compounds, for example substituted imidazolines and oxazolines; phosphorus-containing compounds, for example amine salts of phosphoric acid partial esters or phosphonic acid partial esters, zinc dialkyldithiophosphates; and sulfur-containing compounds, for example barium dinonylnaphthalenesulfonates and calcium petroleumsulfonates.

In certain aspects, the lubricant composition may comprise one or more pour point depressants. The term "pour point depressant" refers to a chemical that lowers the pour point of a liquid, thereby making the liquid flowable at a lower temperature than without the pour point depressant. Suitable examples may include polymethacrylates, polyacrylates, polyacrylamides, alkylated naphthalene derivatives, condensation products of haloparaffin waxes and aromatic compounds, vinyl carboxylate polymers, terpolymers of dialkylfumarates, vinyl esters of fatty acids and alkyl vinyl ethers.

In one or more aspects, the lubricant composition may comprise at least one of an anti-foam agent, a dispersant, and a surfactant. Suitable examples may include silicones or organic polymers, polybutenylsuccinamides or polybutenylsuccinimides, polybutenylphosphonic acid derivatives, and basic magnesium, calcium, and barium sulfonates and phenates.

In one or more embodiments, the lubricant composition may comprise at least one thermal stabilizer. Non-limiting examples of thermal stabilizers include amines, hindered phenols, for example Ethanox® 702, hydroquinone, thioethers, phosphates, sulfur compounds, hydrazines, and any combination thereof.

Additional and alternative additives will be recognized by those skilled in the art given the benefit of this disclosure.

In accordance with certain systems, methods, and compositions, the lubricant composition may comprise one or more of the compounds disclosed herein. One or more of the compounds may be present in the lubricant composition at an amount that does not detract from the functionality of the compound, the composition, or both. In certain aspects, one or more of the compounds disclosed herein may be present in an effective amount to impart one or more desired properties to the lubricant composition. In some aspects, one or more of the compounds may create or further enhance one or more of the properties of the lubricant composition. An effective amount compound, for example, would be a weight percent that is sufficient to impart one or more desired properties to the lubricant composition, given the characteristics of the compound, the specific application for the composition, and the conditions for use. In certain embodiments, an effective amount of compound would be a weight percent that is sufficient to impart one or more desired properties to the lubricant composition, given the characteristics of the compound, the specific application for the composition, and the conditions for use, while not imparting undesired characteristics or reducing one or more desired properties of the lubricant composition. For example, the compound may be present in an amount less than about 2 wt. %. In certain embodiments, one or more compounds disclosed herein may be present in an amount less than about 10 wt. %, less than about 5 wt. %, less than about 3 wt. %, less than about 1 wt. %, or less than about 0.5 wt. % of the lubricant composition. In at least one embodiment, one or more compounds is present in an amount of less than about 5 wt. % of the lubricant composition. In certain embodiments, one or more compounds disclosed herein may be present in an amount of from about 0.01 wt. % to about 10 wt. %, from about 0.01 wt. % to about 5 wt. %, from about 0.01 wt. % to about 3 wt. %, from about 0.01 wt. % to about 1 wt. %, from about 0.01 wt. % to about 0.5 wt. %, or from about 0.01 wt. % to about 0.1 wt. % of the lubricant composition. In various embodiments, the concentration of one or more compounds in the lubricant composition may range from about 0.5% to about 5%. In other examples, the compound may be present in the lubricant composition by an amount greater than about 50% by weight. In various embodiments, one or more compounds disclosed herein may be present in an amount of about 10 wt. % to about 100 wt. % of the lubricant composition. In certain embodiments, one or more compounds disclosed herein may be present in an amount of from about 20 wt. % to about 100 wt. %, from about 40 wt. % to about 100 wt. %, from about 60 wt. % to about 100 wt. %, from about 90 wt. % to about 100 wt. %, or from about 95 wt. % to about 100 wt. % of the lubricant composition. The percent of compound by weight of the lubricant composition may be any percentage or range in between about 0.01% and about 100%. In certain embodiments, the lubricant composition may be 100 wt. % of one or more of the compounds disclosed herein. That is, no carriers or other additives, such as antioxidants, surfactants, or thermal stabilizers are included in the composition. For any application, at least one compound may be used by itself, or used in combination with one or more carriers or additives.

In accordance with one or more embodiments, the systems and methods described herein relate to a method for lubricating at least one surface. The at least one surface may comprise, for example, metals, non-metals such as ceramics, polymers, glass, and synthetics, and any combination thereof. In certain embodiments, the surface may be coated with one or more substances, for example, one or more lubricant compositions known in the art, or one or more compounds and lubricant compositions disclosed herein. In various embodiments, the surface may comprise one or more metals, for example, aluminum, steel, titanium, brass, lead, chrome, cobalt, iron, copper, nickel, silver, gold, tin, tungsten, magnesium, zinc, platinum, and metal alloys. In some embodiments, the surface may comprise one or more varieties of steel, for example stainless steel or any alloy of steel. Non-limiting examples of steel may also include high tensile grades, 304, 440A, 440C, and 52100 stainless steel alloys grades, as well as alloys containing titanium. In one or more embodiments, the surface may be a non-metal, such as a synthetic or man-made surface. In certain aspects, the surface may comprise one or more ceramics. Examples of ceramics may include oxides, nitrides, and carbides of metals. Non-limiting examples of ceramics include titanium oxide, silicon carbide, titanium carbide, silicon nitride, aluminum nitride, cordierite, aluminum titanate, sialon, mullite, silicon nitride, zirconium phosphate, zirconia, titania, alumina, silica, zeolite and LAS (lithium aluminum silicate), graphites, carbon, carbon fibers, fiber reinforced composites, glass ceramics, and any combination thereof. The surface may be any suitable material known in the art for the purposes of performing as a surface as described in the methods and systems disclosed herein.

In accordance with certain aspects, the method may comprise applying a lubricant composition to the at least one surface to form a lubricating layer. As used herein, the term the terms "applying," "apply," "applied," or similar terms refer to any method or technique (including combinations of more than one such method or technique) of applying a material, coating, composition, and the like, including treating, spreading, dabbing, daubing, spraying, brushing, rolling, wiping, and any combination thereof.

The lubricant composition may be provided as discussed and described above. In various embodiments, the lubricant composition may comprise at least one compound represented by the above-described formula (I) and each of the groups Y and $X_n$ independently include the meanings set forth in the previous sections to the extent that they are consistent with the above descriptions and definitions.

The term "lubricating layer" refers to a layer of material of a thickness sufficient to prevent at least a portion of a first surface from directly contacting at least a portion of a second surface. In certain embodiments, the thickness of the lubricating layer may be greater than the maximum surface roughness of at least a portion of the first surface, at least a portion of the second surface, or both. In certain aspects, the lubricating layer may be one monolayer in thickness. In other aspects, the lubricating layer may be several monolayers in thickness.

In at least one aspect, the lubricating layer is provided in the form of a monolayer. The term "monolayer" refers to a single layer of material. In some embodiments, the single layer may be comprised of atoms, molecules, or a combination thereof. In certain embodiments, the monolayer may be substantially uniform in thickness, although slight variations of between approximately zero to five monolayers may result in an average of a single monolayer as used in the systems and methods described herein. In certain other embodiments, the monolayer may comprise a layer of molecules with head groups, such as a 2,4,6-trimethyl group, substantially aligned on one side and a hydrocarbon moiety substantially on the opposite side.

In certain embodiments, the method may further comprise continuously providing the lubricant composition to the at least one surface. The term "continuously," with respect to providing the lubricant composition, may refer to being constant or without interruption, or refer to an incremental addition that provides substantially the same results as constantly providing the lubricant composition. In certain aspects, the lubricating layer may be continuously sustained and renewed. In certain aspects, the lubricating layer may be continuously renewed by deposition of the lubricant composition. In other aspects, continuously providing the lubricant composition may prevent local heating or overheating on at least one surface. In certain embodiments, the lubricant composition may be configured to continuously provide the lubricating layer to the at least one surface, that is, the lubricant composition may provide for continuous renewal of the lubricating layer without an outside source and with minimal evaporation of the lubricant composition. In certain other embodiments, the lubricant composition may be continuously provided with the aid of an outside source, such as a distribution system.

In accordance with the methods, systems and compositions herein, the lubricant composition may reduce a coefficient of friction of at least one surface. In certain aspects, continuously providing the lubricant composition reduces a coefficient of friction of the at least one surface. Reducing the coefficient of friction of the at least one surface may refer to providing an amount of lubricant composition comprising one or more compounds disclosed herein that is effective to reduce the coefficient of friction of the at least one surface when compared to a lubricant composition without the one or more compounds disclosed herein. The terms "reduced," "reducing," or "reduction" when used in reference to the compositions comprising at least one compound disclosed herein and the coefficient of friction of a surface, may refer to any reduction in the coefficient of friction as compared to a composition without the at least one compound disclosed herein. According to certain aspects, the coefficient of friction is reduced by at least about 50%, versus a lubricant composition without the at least one compound according to the formula (I). In another aspect, the coefficient of friction is reduced by at least about 40%, by at least about 30%, by at least about 20%, by at least about 10%, or by at least about 5%, versus a lubricant composition without the at least one compound according to the formula (I).

In certain aspects, continuously providing the lubricant composition to the at least one surface reduces wear of the least one surface. According to a further aspect, a reduction in wear of the least one surface is greater than a reduction in wear of the at least one surface using a lubricant composition without the at least one compound according to the formula (I).

Without being bound by theory, it is postulated that the compounds disclosed herein may interact with at least one surface to provide a protective film or layer on the surface that possesses a lower shear strength than the surface. The compounds function to reduce friction temperatures and allow the film or layer to remain on the surface. When raised points of mating surfaces come in contact with each other, the lower shear strength of the protective film or layer may cause the film or layer to shear, rather than fuse and cause scoring. Therefore, one or more of the compounds disclosed herein may serve to control wear on one or more surfaces.

According to a further aspect, the method may further comprise removing at least a portion of the lubricating layer from the at least one surface. The term "at least a portion" refers to some, or all, of the surface or material being described. Thus, in certain aspects, some, or all, of the lubricating layer may be removed from the at least one surface.

According to another aspect, the lubricant composition continuously provides the lubricating layer to at least a portion of the at least one surface. Without being bound by theory, it is postulated that electronegative moieties, such as the carbonyl oxygen atom on the compounds disclosed herein, may coordinate to one or more surfaces in a non-covalent manner. The non-covalent bonding may enhance the interchange of molecules at the monolayer level along the surface. In certain aspects, this capability may allow for a continuous lubrication scheme where functional groups or compounds that suffer breakdown at the monolayer level may be continuously replenished. In various aspects, migration of the compound may be driven by locally derived chemical potential gradients.

According to yet another aspect, the method further comprises providing a distribution system. As used herein, the term "distribution system" refers to structures through which fluids are delivered to a desired location. The distribution system may comprise, for example, one or more pump assemblies, one or more dispensers, such as a syringe or spray assembly, one or more reservoirs to store one or more fluids being dispensed, and one or more valves, tubes, pipes, or conduits. In some aspects, the distribution system may be in communication with a source of the lubricant composition. For example, the distribution system may be in communication with a reservoir that holds one or more lubricant compositions. In a further aspect, the distribution system may be in communication with at least one surface. In yet another aspect, the distribution system may be configured to continuously provide an aliquoted amount of the lubricant composition to at least a portion of at least one surface. For example, a single drop of the lubricant composition may be placed at a desired location on the surface, multiple drops may be placed in a line or an array, or a single bead may be placed in a line or an array. The lubricant composition may also be extruded. In addition, a film of the lubricant composition may be applied to the surface by using one or more sprayers or brushes. The composition may also be deposited in increments to build up a layer or layers of material.

In certain aspects, the distribution system may be configured to continuously provide the lubricant composition for a predetermined period of time. As used herein, the term "predetermined period of time" represents an interval of time. For example, the interval of time may be seconds, minutes, hours, days, months, or years. The predetermined period of time may be any interval of time that is suitable for the purposes of the methods and systems disclosed herein.

In a further aspect, the method may further comprise providing a control system. The term "control system" may refer to a combination of devices and software operative to manage, command, direct, or regulate the behavior of other devices, equipment or systems. The control system may comprise, for example, one or more monitoring devices for detecting one or more substances, such as one or more of the compounds or lubricant compositions disclosed herein. In certain aspects, one or more of the compounds disclosed herein may break down into products or produce by-products that emit identifiable signatures that aid in their detection. For example, IR analytical techniques may be applied to provide for monitoring the concentration of at least one of the compound, the composition, and the respective breakdown products or by-products. The control system may be configured to provide for local and remote monitoring.

In accordance with one or more embodiments, the systems and methods disclosed herein relate to a method for reducing at least one of a rate of wear and a coefficient of friction during operation of a mechanical apparatus comprising at least one surface. As used herein, the term "during operation," when used in reference to a mechanical apparatus, refers to one or more operational modes where the mechanical apparatus is in use. As used herein, the term "mechanical apparatus" refers to any machine, apparatus, device, or the like that converts one form of mechanical energy into another. Non-limiting examples of a mechanical apparatuses include compressors, pumps, blowers, robots, exercise equipment, automated equipment, medical devices, electronic devices, pivoting devices, turbines, guidance systems, vacuum assemblies, construction equipment, computer systems, motors, engines, power stations, and reactors. The mechanical apparatus may be any suitable apparatus known in the art for the purposes of performing the methods and systems disclosed herein.

In certain embodiments, the mechanical apparatus may be a turbine. Non-limiting examples of turbines include hydroelectric turbines, gas turbines, compressors, and wind turbines. In one or more embodiments, the turbine may be a wind turbine. In certain embodiments, the mechanical apparatus may be an engine. Non-limiting examples of engines include internal combustion engines, electric motors, solar energy converters, nuclear power plants, and hybrid systems that combine two or more different types of energy conversion processes. In one or more embodiments, the mechanical apparatus may be an internal combustion engine. Non-limiting examples of internal combustion engines include gasoline and diesel engines, Wankel engines, jet engines, rocket engines, and gas turbine engines. In one or more embodiments, the mechanical apparatus may be a transportation device. Non-limiting examples of transportation devices include vehicles such as automobiles, trains, trucks, all-terrain, motorized cycles, trolleys and trams, skateboards, bicycles, boats, airplanes, buses, and military vehicles, elevators, escalators, fork-lifts, golf carts, wheelchair lifts, dumbwaiters, sidewalk lifts, man-lifts, moving walkway systems, roller hoist systems, crane systems, conveyer systems, and cargo systems.

In various embodiments, the mechanical apparatus may be a guidance system. The guidance system may be any system used to control or guide an external object to a desired location or along a desired path. For example, a guidance system may be used for guiding a rocket or missile on its trajectory to a target. In other embodiments, the guidance system may be used for landing an aircraft. In at least one embodiment, the guidance system is a precision mechanical system, for example, high precision accelerometers and gyroscopes.

In accordance with certain aspects, the method comprises adding a lubricant composition to at least one surface of the mechanical apparatus. In various aspects, the lubricant composition may be added to at least one surface of one or more components of a mechanical apparatus. For example, the lubricant composition may be added to at least one surface of gears, shafts, crankcases, or bearings of a mechanical apparatus. The lubricant composition may be provided as discussed and described above. In various embodiments, the lubricant composition may comprise at least one compound represented by the above-described formula (I) and each of the groups Y and $X_n$ independently include the meanings set forth in the previous sections to the extent that they are consistent with the above descriptions and definitions.

According to a further aspect, at least one surface of the mechanical apparatus exhibits a reduction in the rate of wear. According to another aspect, at least one surface of the mechanical apparatus exhibits a percent reduction in the coefficient of friction. In certain aspects, the reduction in the coefficient of friction may be at least about 50%, versus a lubricant composition without the at least one compound according to formula (I). In another aspect, the coefficient of friction is reduced by at least about 40%, by at least about 30%, by at least about 20%, by at least about 10%, or by at least about 5%, versus a lubricant composition without the at least one compound according to formula (I).

In accordance with one or more embodiments, the systems and methods disclosed herein relate to a method for facilitating the operation of a mechanical apparatus. In certain embodiments the method comprises providing a lubricant composition. The lubricant composition may be provided and characterized as previously discussed. In various embodiments, the lubricant composition may comprise at least one compound represented by the above-described formula (I) and each of the groups Y and $X_n$ independently include the meanings set forth in the previous sections to the extent that they are consistent with the above descriptions and definitions.

In at least one aspect, the method may further comprise providing instructions for applying the lubricant composition to the mechanical apparatus. In certain aspects, providing instructions may include providing at least one instruction to apply the lubricant composition to at least one surface of a mechanical apparatus. In various aspects, providing instructions may include providing instructions to replace a pre-existing lubricant composition with one or more of the lubricant compositions disclosed herein. As used herein, the term "pre-existing," refers to a lubricant composition that does not comprise at least one compound according to formula (I). In one or more aspects, providing instructions may include providing instructions to add to a pre-existing lubricant composition with one or more of the lubricant compositions disclosed herein.

In one or more aspects, the method of facilitating may comprise replacing a pre-existing lubricant composition with one or more of the lubricant compositions disclosed herein. In other aspects, the method of facilitating may comprise using one or more of the lubricant compositions disclosed herein together with a pre-existing lubricant composition. In certain aspects, the method may comprise applying one or more of the lubricant compositions disclosed herein to one or more surfaces of a mechanical apparatus. In various aspects, the method may comprise introducing at least one or more of the lubricant compositions disclosed herein to one or more surfaces of a mechanical apparatus.

The invention contemplates the modification of existing facilities to retrofit one or systems or components in order to implement the techniques of the invention. For example, an existing mechanical apparatus may be modified in accordance with one or more embodiments exemplarily discussed herein utilizing at least some of the preexisting components. One or more surfaces may be provided and a lubricant composition in accordance with one or more embodiments presented herein may be implemented in a preexisting mechanical apparatus to promote lubrication.

EXAMPLES

Example 1

Ball-on-disc Wear Tests to Determine Coefficient of Friction

Standard material wear testing was performed to determine the anti-wear properties of several different lubricant compositions. Ball-on-disc wear tests were performed using a single ball on a CETR UMT-2 tribometer (Bruker Corp., Campbell, Calif.) in accordance with ASTM G99-05. A DURASYN® 174 lubricant, (INEOS Oligomers, League City, Tex.) was used as the base lubricant, and 5 wt. % lubricant compositions were created from TCP, mesityl tetradecanoate, and mesityl 3,3-dimethylbutanoate. A single, 4 mm (5/32") diameter weighted ball was placed in contact with a highly polished rotating metal disc. The disc and ball were made from 440C stainless steel, with a hardness value between 59-61 on the Rockwell C scale. The force exerted normal to the disk surface was 40 N (9 lbs), and the disk was rotated at 240 rpm. Tests were performed at 40° C. on the lubricant compositions and the appropriate control. The test duration in each case was for a period of 23 hours, with measurements taken continuously. FIG. 1 graphically illustrates the measured values for the coefficient of friction taken for each sample during the course of the 23-hour test. The frictional response for TCP was characterized by an initial break-in period that was followed by a period of steady-state wear. Table 1 below presents the results from the wear tests.

TABLE 1

Results from Ball-on-Disc Wear Test

| Lubricant Composition | Average COF | Low COF Value | High COF Value | Percent Reduction in Average COF (compared to the DURASYN ® 174 lubricant control) |
|---|---|---|---|---|
| DURASYN ® 174 lubricant | .076 | .067 | .088 | 0 |
| 5% TCP | .049 | .033 | .051 | At least 30% reduction |
| 5% mesityl tetradecanoate | .039 | .032 | .041 | At least 40% reduction |
| 5% mesityl 3,3-dimethylbutanoate | .033 | .033 | .038 | At least 50% reduction |

As illustrated by the experimental results presented in FIG. 1 and Table 1, both the 5% mesityl tetradecanoate and the 5% mesityl 3,3-dimethylbutanoate lubricant compositions have the lowest coefficient of friction values and appear to be more effective at reducing friction than the conventional additive, TCP. That is, these compounds have a lower measure of sliding resistance of one material over another material, as compared to TCP. Both compounds also outperformed the DURASYN® 174 lubricant.

Example 2

Ball-on-disc Wear Tests to Determine Mechanical Wear Characteristics

The ball-on-disc wear tests described in Example 1 were also used to determine the mean wear scar diameters of several compositions, including those tested in Example 1. The DURASYN® 174 lubricant was used as the base lubricant, and 5 wt. % lubricant compositions were prepared from TCP, mesityl tetradecanoate, and mesityl 3,3-dimethylbutanoate, and a 1 wt. % composition was prepared from 1,10-dimesityl sebacylate. The mean wear scar diameters for each of the above samples were measured using a scanning electron microscope (SEM) (Zeiss Supra 35VP, Carl Zeiss, Inc. Peabody, Mass.). Wear scar measurements that are low in value are indicative of compositions possessing better lubricity. Table 2 presents the wear scar measurement results from the experiment.

TABLE 2

Wear Scar Measurements from Ball-on-Disc Wear Test

| Lubricant Composition | Scar Width Measurement (μm) |
| --- | --- |
| 5% TCP | 550 |
| 5% mesityl tetradecanoate | 325 |
| 5% mesityl 3,3-dimethylbutanoate | 285 |
| 1% 1,10-dimesityl sebacylate | 420 |

Figure 2:
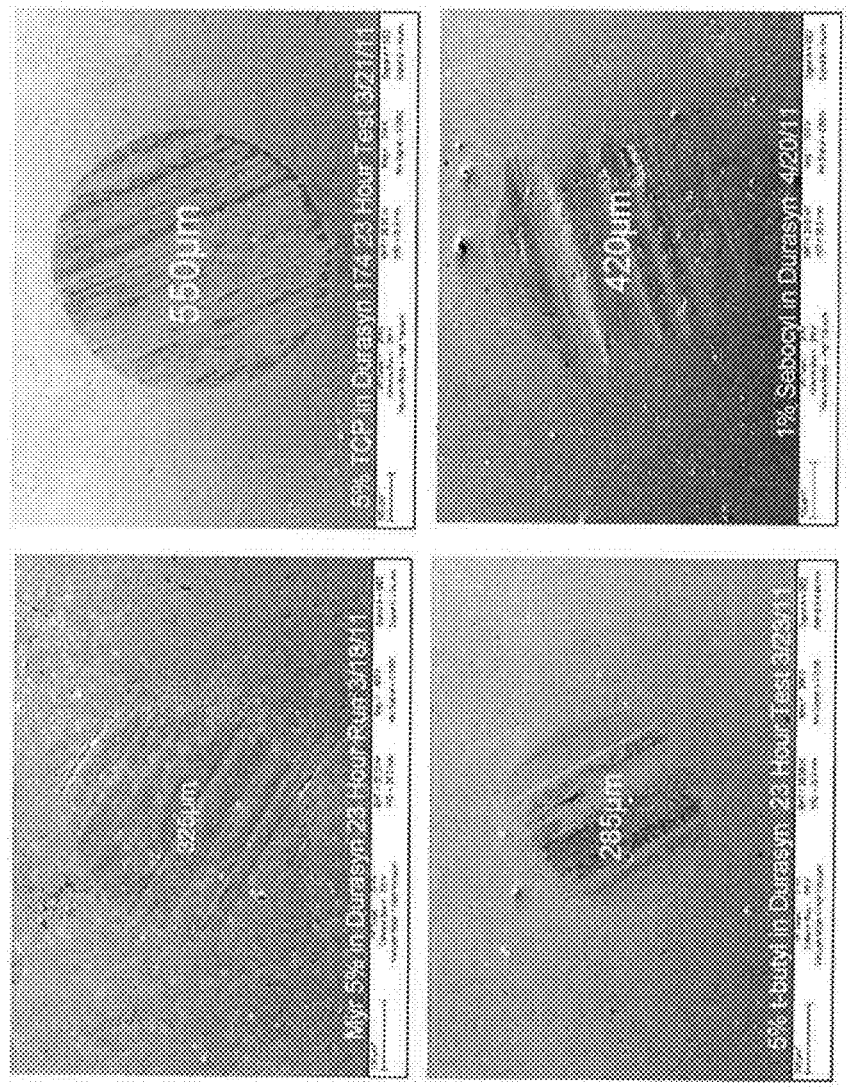
FIG. 2 is an illustration of the results of tests performed in accordance with aspects of the present disclosure.

As illustrated by the experimental results presented in Table 2, the compounds made in accordance with the methods and systems described herein appear to be more effective anti-wear lubricants than the conventional additive, TCP. In particular, the 1,10-dimesityl sebacylate composition was found to be more effective as an anti-wear lubricant than the TCP composition, even when present in only a 1% concentration. FIG. 2 shows a general view of wear marks observed under the SEM upon completion of the wear test experiments. The results indicate that the 5% mesityl 3,3-dimethylbutanoate composition had the least degree of wear, while wear marks of the TCP had the maximum width and the most serious damage. Both the 1% 1,10-dimesityl sebacylate and the 5% mesityl 3,3-dimethylbutanoate also showed less wear than the TCP composition.

Example 3

Thermogravimetric Analysis Tests to Determine Thermal Stability

Figure 3:
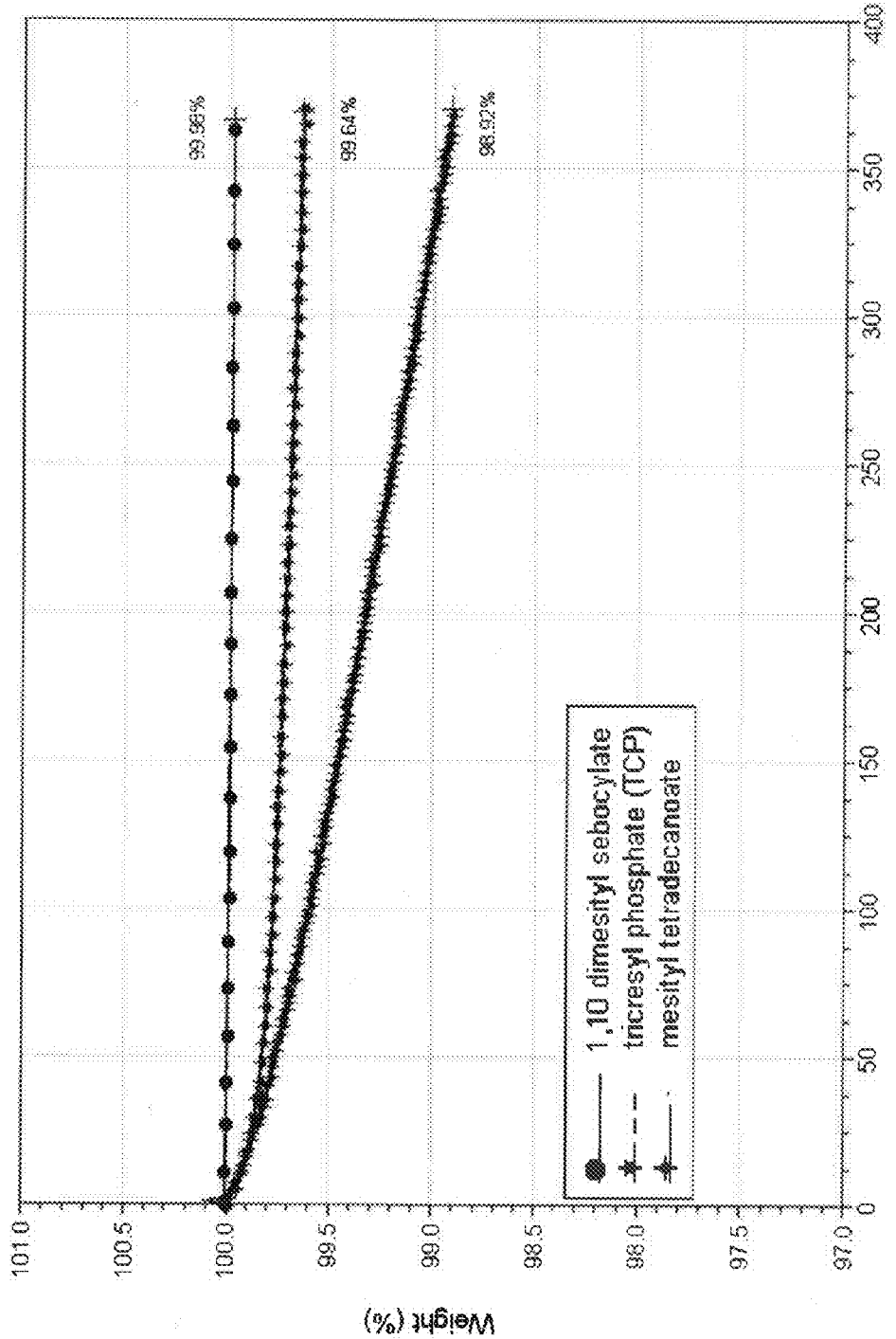
FIG. 3 is a graphic illustration of the results of tests performed in accordance with aspects of the present disclosure.

Thermogravimetric analysis (TGA) was performed to characterize the thermal stability of several of the compounds made in accordance with the methods and systems described herein. Thermogravimetric analysis tests were performed using a TGA 500 (TA Instruments, New Castle, Del.). Samples of 1,10-dimesityl sebacylate, TCP, and mesityl tetradecanoate were prepared and heated. The samples were heated from room temperature to 100° C., the temperature at which they remained for a period of 6 hours. FIG. 3 graphically depicts the TGA results from the three samples. Results from the test indicate that the 1,10-dimesityl sebacylate appears to be more thermally stable than the conventional additive, TCP. After about 375 minutes, mesityl tetradecanoate showed 98.92% of the original weight, TCP showed 99.64% of the original weight, and 1,10-dimesityl sebacylate showed 99.98% of the original weight.

Figure 4:
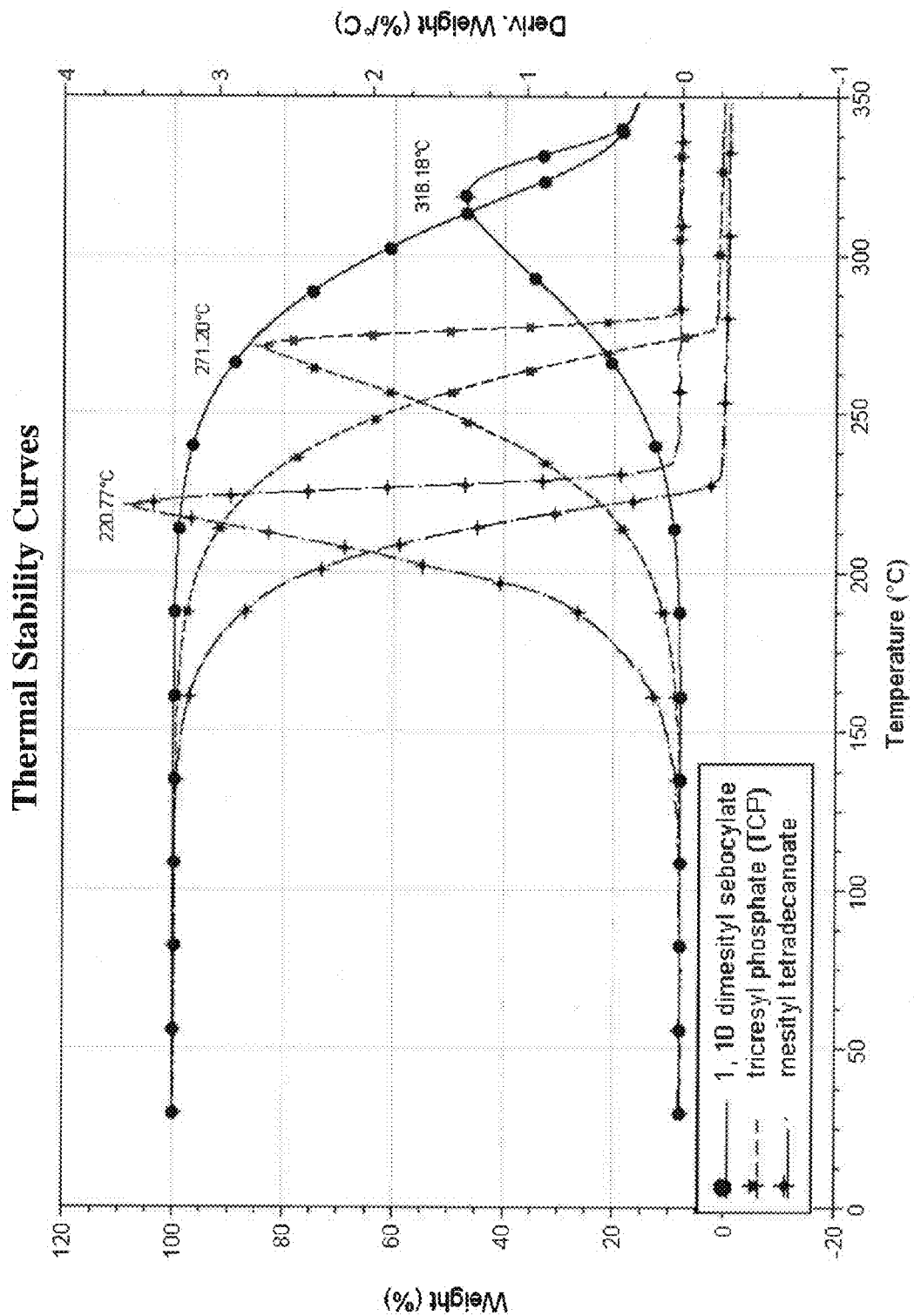
FIG. 4 is a graphic illustration of the results of tests performed in accordance with aspects of the present disclosure.

TGA tests were also performed to determine decomposition curves for the various samples. The temperature was ramped from an initial value of 30° C. to 350° C. at a rate of 5° C./min. The results are graphically illustrated in FIG. 4. The maximum differential weight change for 1,10-dimesityl sebacylate appeared at 318.2° C., outperforming TCP by about 50° C., where the peak appeared at 271.20° C. The results from this test also indicate that at higher temperatures the rate of loss of the 1,10-dimesityl sebacylate is extended when compared to the rapid and complete loss of TCP under the same conditions.

Example 4

Preparation of Mesityl Tetradecanoate

This example illustrates the method used for the preparation of mesityl tetradecanoate. A 400 ml three neck flask was charged with 73 millimoles (mmol) of pyridine, 37 mmol of 2,4,6-trimethyl phenol, and 100 ml of dichloromethane (DCM). The solution was cooled to −10° C. While cooling, 37 mmol of myristoyl chloride was mixed with 50 ml of DCM and added to a pressure equalized dripping funnel. The dripping funnel was attached to one of the three necks (the center) of the flask, while the remaining two necks of the flask were fitted with a calcium chloride ($CaCl_2$) drying tube and a rubber septum. The myristoyl chloride solution was added dropwise into the three neck flask over a period spanning about 60 minutes while the contents of the flask were continuously stirred with the aid of a magnetic stirrer. The resulting solution was stirred overnight at room temperature (approx. 16 hours). The rough product was purified using standard methods of silica gel column chromatography to produce a final product with greater than 95% purity. Excess solvent was discharged from the product using rotary evaporative methods.

Example 5

Preparation of Mesityl 3,3-dimethylbutanoate

This example illustrates the method used for the preparation of mesityl 3,3-dimethylbutanoate. A 500 ml three neck round bottom flask was charged with 0.0367 moles (mol) of 2,4,6-trimethyl phenol, 0.0734 mol of triethylamine, and 400 ml of tetrahydrofuran (THF). A mixture of 0.0477 mol of t-butylacetyl chloride and 50 ml of THF was added to a pressure equalized dripping funnel. The dripping funnel was attached to one of the three necks (the center) of the flask, while the remaining two necks of the flask were fitted with a calcium chloride ($CaCl_2$) drying tube and a rubber septum. The t-butylacetyl chloride solution was slowly added dropwise into the three neck flask and kept at ambient temperature while using a magnetic stirrer to continuously mix the contents of the flask. The resulting solution was left to stir overnight (approx. 16 hours). A triethylamine salt formed during the course of the reaction as a reaction byproduct. The salt was removed from the mixture using standard vacuum filtration methods while the remaining contents of the flask (containing the product) were collected. The product was purified using standard methods of silica gel column chromatography to produce a final product with greater than 95% purity and about 50% yield. Excess solvent was discharged from the product using rotary evaporative methods.

Example 6

Preparation of Mesityl Dimethylcarbamate

This example illustrates the method used for the preparation of mesityl dimethylcarbamate. A 500 ml three neck round bottom flask was charged with 0.036 moles (mol) of 2,4,6-trimethyl phenol, 0.072 mol of triethylamine, and 400 ml of THF. A mixture of 0.046 mol of dimethyl carbamyl chloride and 50 ml of THF was added to a pressure equalized dripping funnel. The dripping funnel was attached to one of the three necks (the center) of the flask, while the remaining two necks of the flask were fitted with a calcium chloride ($CaCl_2$) drying tube and a rubber septum. The dimethyl carbamyl chloride solution was slowly added dropwise into the contents of the three neck flask and kept at ambient temperature while using a magnetic stirrer to continuously mix the contents of the flask. The resulting solution was left to stir overnight (approx. 16 hours). A triethylamine salt formed during the course of the reaction as a reaction byproduct. The salt was removed from the mixture using standard vacuum filtration methods while the remaining contents of the flask (containing the product) were collected. The product was purified using standard methods of silica gel column chromatography to produce a final product with greater than 95% purity. Excess solvent was discharged from the product using rotary evaporative methods.

Example 7

Preparation of Mesityl Diphenylcarbamate

This example illustrates the method used for the preparation of mesityl diphenylcarbamate. A 500 ml three neck round bottom flask was charged with 0.018 moles (mol) of 2,4,6-trimethyl phenol, 0.036 mol of triethylamine, 4 ml pyridine, and 400 ml of THF. A mixture of 0.046 mol of diphenyl carbamyl chloride and 50 ml of THF was added to a pressure equalized dripping funnel. The dripping funnel was attached to one of the three necks (the center) of the flask, while the remaining two necks of the flask were fitted with a calcium chloride ($CaCl_2$) drying tube and a rubber septum. The diphenyl carbamyl chloride solution was slowly added dropwise into the contents of the three neck flask and kept at ambient temperature while using a magnetic stirrer to continuously mix the contents of the flask. The resulting solution was left to stir overnight (approx. 16 hours). A triethylamine salt formed during the course of the reaction as a reaction byproduct. The salt was removed from the mixture using standard vacuum filtration methods while the remaining contents of the flask (containing the product) were collected. The product was purified using standard methods of silica gel column chromatography to produce a solution with greater than 90% purity. Excess solvent was discharged from the product using rotary evaporative methods.

Example 8

Preparation of 1,10-dimesityl Sebacylate

This example illustrates the method used for preparing 1,10-dimesityl sebacylate. A 500 ml three neck round bottom flask was charged with 0.0585 moles (mol) of 2,4,6-trimethyl phenol, 0.0878 mol of triethyl amine, and 400 ml of THF. A mixture of 0.029 mol of sebacoyl chloride and 50 ml of THF was added to a pressure equalized dripping funnel. The dripping funnel was attached to one of the three necks (the center) of the flask, while the remaining two necks of the flask were fitted with a calcium chloride ($CaCl_2$) drying tube and a rubber septum. The sebacoyl chloride solution was slowly added dropwise into the contents of the three neck flask and kept at ambient temperature while using a magnetic stirrer to continuously mix the contents of the flask. The resulting solution was left to stir overnight (approx. 16 hours). A triethylamine salt formed during the course of the reaction as a reaction byproduct. The salt was removed from the mixture using standard vacuum filtration methods while the remaining contents of the flask (containing the product) were collected. The product was purified using standard methods of silica gel column chromatography to produce a solution with greater than 95% purity and about 40% yield.

The systems and methods described herein are not limited in their application to the details of construction and the arrangement of components set forth in the description or illustrated in the drawings. The invention is capable of other embodiments and of being practiced or of being carried out in various ways. Also, the phraseology and terminology used herein is for the purpose of description and should not be regarded as limiting. The use of "including," "comprising," "involving," "having," "containing," "characterized by," "characterized in that," and variations thereof herein is meant to encompass the items listed thereafter, equivalents thereof, as well as alternate embodiments consisting of the items listed thereafter exclusively. Use of ordinal terms such as "first," "second," "third," and the like in the claims to modify a claim element does not by itself connote any priority.

Those skilled in the art would readily appreciate that the various parameters and configurations described herein are meant to be exemplary and that actual parameters and configurations will depend upon the specific application for which the compounds, lubricant compositions, and systems and methods directed toward the same of the present disclosure are used. Those skilled in the art will recognize, or be able to ascertain using no more than routine experimentation, many equivalents to the specific embodiments described herein. For example, those skilled in the art may recognize that the compounds, lubricant compositions, and systems and methods directed toward the same may be a component of a process using lubricant compositions. It is, therefore, to be understood that the foregoing embodiments are presented by way of example only and that, within the scope of the appended claims and equivalents thereto, the disclosed compounds, lubricant compositions, and systems and methods directed toward the same may be practiced otherwise than as specifically described. The present methods are directed to each individual feature or method described herein. In addition, any combination of two or more such methods, if such methods are not mutually inconsistent, is included within the scope of the present disclosure.

Further, it is to be appreciated various alterations, modifications, and improvements will readily occur to those skilled in the art. Such alterations, modifications, and improvements are intended to be part of this disclosure, and are intended to be within the spirit and scope of the disclosure. For example, an existing facility or process may be modified to utilize or incorporate any one or more aspects of the disclosure. Thus, in some cases, the apparatus and methods may involve connecting or configuring an existing facility to comprise one or more of the compounds, lubricant compositions, and systems and methods directed toward the same. Accordingly, the foregoing description and figures are by way of example only.

Further, the depictions in the figures do not limit the disclosures to the characteristics of the particularly illustrated representations.

While exemplary embodiments of the disclosure have been disclosed, many modifications, additions, and deletions may be made therein without departing from the spirit and scope of the disclosure and its equivalents, as set forth in the following claims.

What is claimed is:

1. A compound comprising a formula:

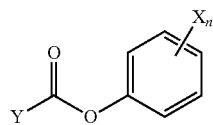

wherein:
$X_n$ represents $CH_3$ or heteroatom, and n is 3;
Y represents
  $(C_1-C_{30})$alkyl, or
  heteroaryl,
wherein $(C_1-C_{30})$ alkyl and heteroaryl are substituted with 0-3 occurrences of $R^4$; and
$R^4$ represents
  $(C_1-C_6)$alkyl,
  $(C_1-C_6)$alkoxy,
  aryl, or
  heteroaryl.

2. The compound of claim 1, wherein Y represents $(C_1-C_{30})$alkyl,
wherein $(C_1-C_{30})$alkyl is substituted with 0-1 occurrences of $R^4$; and
$R^4$ represents
  $(C_1-C_6)$alkyl, or
  $(C_1-C_6)$alkoxy.

3. The compound of claim 2, wherein Y represents $(C_1-C_{30})$alkyl substituted with 0-1 occurrences of $(C_1-C_6)$alkyl.

4. The compound of claim 3, wherein $(C_1-C_{30})$alkyl is substituted with zero occurrences of $R^4$.

5. The compound of claim 4, wherein Y represents $-CH_2(CH_2)_{11}CH_3$ and n is substituted in the 2,4,6-positions.

6. The compound of claim 4, wherein Y represents $-CH_2C(CH_3)_3$ and n is substituted in the 2,4,6-positions.

* * * * *